(12) United States Patent
Hsieh et al.

(10) Patent No.: US 7,558,363 B2
(45) Date of Patent: Jul. 7, 2009

(54) STEP-AND-SHOOT CARDIAC CT IMAGING

(75) Inventors: Jiang Hsieh, Brookfield, WI (US); Jianying Li, Beijing (CN); Melissa L. Vass, Milwaukee, WI (US); Xiangyang Tang, Waukesha, WI (US); Darin Robert Okerlund, Muskego, WI (US); Bernice E. Hoppel, Delafield, WI (US); Kelly Ann Mohr, Beaverton, OR (US); John Howard Londt, Lafayette, IN (US)

(73) Assignee: General Electric Company, Schenectady, NY (US)

( * ) Notice: Subject to any disclaimer, the term of this patent is extended or adjusted under 35 U.S.C. 154(b) by 130 days.

(21) Appl. No.: 11/941,219

(22) Filed: Nov. 16, 2007

(65) Prior Publication Data

US 2008/0063137 A1  Mar. 13, 2008

Related U.S. Application Data

(63) Continuation-in-part of application No. 11/160,028, filed on Jun. 6, 2005, now Pat. No. 7,313,213.

(51) Int. Cl.
*G01N 23/083* (2006.01)
*H05G 1/62* (2006.01)
(52) U.S. Cl. .................. 378/8; 378/19; 378/20
(58) Field of Classification Search .......... 378/8, 378/19, 20, 95; 600/428
See application file for complete search history.

(56) References Cited

U.S. PATENT DOCUMENTS

| | | | |
|---|---|---|---|
| 6,721,386 B2 | 4/2004 | Bulkes et al. | |
| 6,836,529 B2 | 12/2004 | Li et al. | |
| 7,020,511 B2 * | 3/2006 | Boyd et al. | 600/428 |
| 7,058,440 B2 * | 6/2006 | Heuscher et al. | 600/428 |
| 7,251,308 B2 | 7/2007 | Tsuyuki | |
| 7,313,213 B1 * | 12/2007 | Hsieh et al. | 378/8 |
| 2003/0152189 A1 | 8/2003 | Li et al. | |
| 2003/0161436 A1 | 8/2003 | Boyd et al. | |
| 2004/0077941 A1 | 4/2004 | Reddy et al. | |

* cited by examiner

*Primary Examiner*—Edward J Glick
*Assistant Examiner*—Thomas R Artman

(57) ABSTRACT

A CT imaging system includes a gantry and a table in a movable relationship with the gantry. The CT imaging system also includes a controller configured to control relative movement between a subject disposed on the table and the gantry from a first data acquisition position to a second data acquisition position. The controller is also configured to determine a total scan time based on a first time for acquiring imaging data at the first data acquisition position and a second time for transitioning from the first data acquisition position to the second data acquisition position. The controller is also configured to disable data acquisition in an immediately subsequent cardiac cycle and re-enable data acquisition in the cardiac cycle following the immediately subsequent cardiac cycle if the total scan time exceeds one cardiac cycle of the subject. A method of CT imaging is also disclosed.

15 Claims, 5 Drawing Sheets

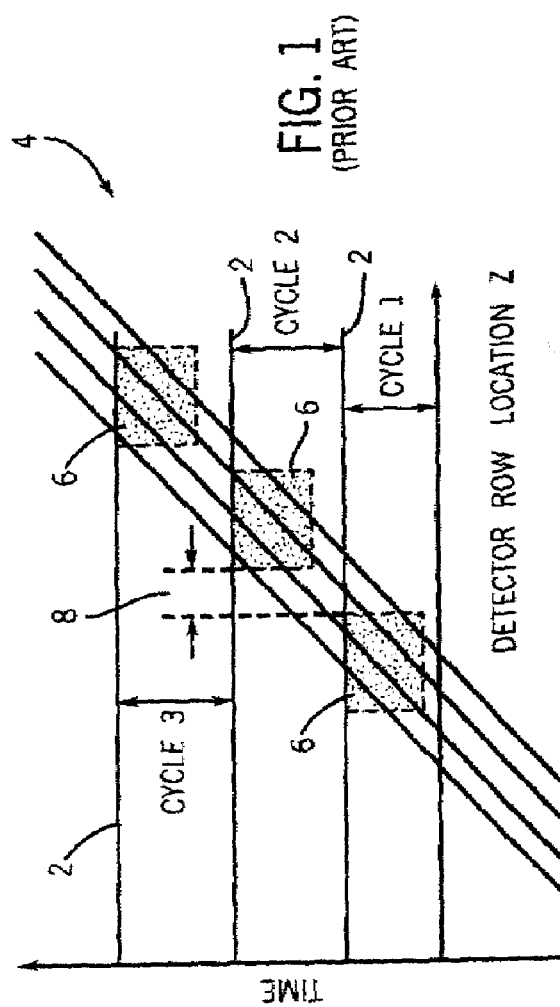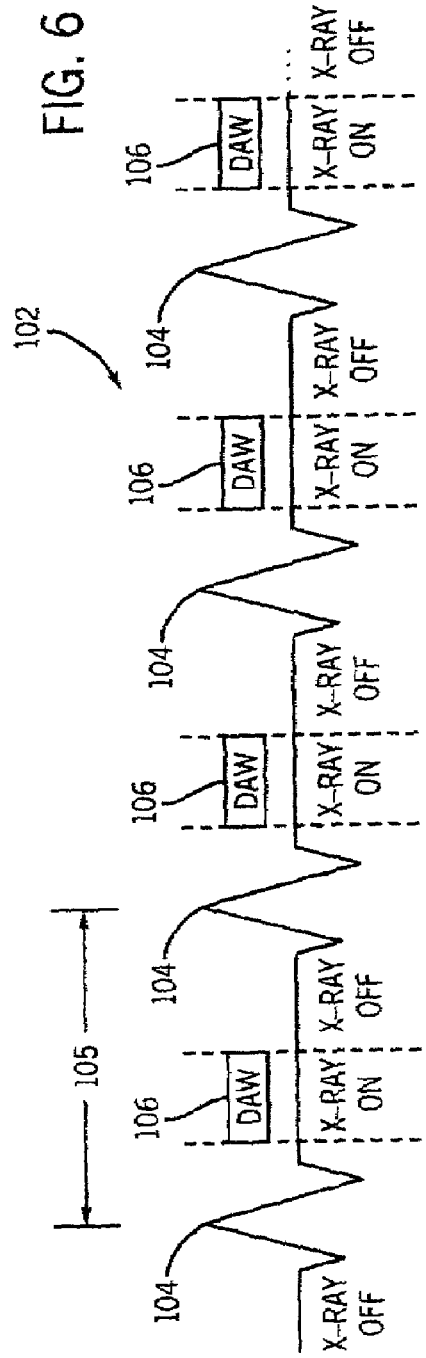

STEP-AND-SHOOT CARDIAC CT IMAGING

CROSS REFERENCE TO RELATED APPLICATIONS

This application is a continuation in part of U.S. patent application Ser. No. 11/160,028 filed Jun. 6, 2005. The application is incorporated herein by reference.

BACKGROUND OF THE INVENTION

The narrowing or constriction of vessels carrying blood to the heart is a well-known cause of heart attacks and, gone untreated, can lead to sudden death. In such stenotic vessels, it is known that the region immediately downstream from the constriction is characterized by having rapid flow velocities and/or complex flow patterns. In general, narrowing of blood carrying vessels supplying an organ will ultimately lead to compromised function of the organ in question, at best, and organ failure, at worst. Quantitative flow data can readily aid in the diagnosis and management of patients and also help in the basic understanding of disease processes. There are many techniques available for the measurement of blood flow, including imaging based methods using radiographic imaging of contrast agents, both in projection and computed tomography (CT), ultrasound, and nuclear medicine techniques. Radiographic and nuclear medicine techniques often require the use of ionizing radiation and/or contrast agents. Some methods involve making assumptions about the flow characteristics which may not necessarily be true in vivo or require knowledge about the cross-sectional area of the vessel or the flow direction.

CT is one technique of acquiring blood flow and other cardiac data. Typically, in CT imaging systems, an x-ray source emits a fan-shaped beam or cone-shaped beam toward a subject or object. Hereinafter, reference to a "subject" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image. Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Increasingly, CT imaging is being used for cardiac imaging. This increase in the implementation of CT for cardiac imaging is primarily predicated upon the relatively fast scan speeds that are now possible with CT systems and the acquisition of multi-slice data. Conventional CT systems are now capable of supporting 0.35 seconds per gantry rotation, if not faster. In fact, in the past decade, there has been nearly a three-fold improvement in temporal resolution. Multi-slice CT acquisition has also contributed to the rise of cardiac CT imaging for cardiac-related diagnoses. CT systems are now capable of significant multi-slice acquisitions.

One application of cardiac CT imaging is coronary artery imaging (CAI). The objective of CAI is to capture images and thus visualize the vasculature of the heart to detect vascular narrowing, disease, or anomalies. CAI is often used by cardiologists, radiologists, and other physicians to examine the dynamic motion of the heart muscles to detect abnormalities. To visualize the narrowing or constriction of a small vessel, the CT scan must provide high temporal resolution so as to "freeze" the cardiac motion in and around the vessel as well as provide high spatial resolution to accurately depict the size of the vessel under examination.

To improve temporal resolution, CAI studies are typically carried out with the assistance of electrocardiogram (ECG) signals acquired from the patient using an ECG monitor. An ECG monitor records the electrical activity of the heart using electrodes placed on the patient's chest, arms, and legs. An ECG monitor is commonly used to provide information regarding heart rate, heart rhythm, adequacy of blood supply to the heart, presence of a heart attack, enlargement of the heart, pericarditis, and the effects of drugs and electrolytes on the heart. ECG signals may also be used to provide cardiac phase data so as to synchronize the acquisition of CT data from the heart with the phase activity of the heart. More particularly, the CT system uses the ECG signals to consistently acquire data during the same phase of the cardiac cycle during the CT scan. Doing so reduces image artifacts.

In conventional helical CAI scans, the table translates the patient continuously at a relatively slow pace, i.e. low-pitch, to ensure that the entire heart volume is properly covered. This is illustrated in FIG. 1 where detector row position as a function of time is plotted. As shown, the cardiac cycles are separated by horizontal dotted lines 2. The detector-row locations are depicted by the solid diagonal lines 4. Every point on these lines represents a single-row projection collected at a certain z location and a particular time (therefore a particular projection angle). The z-axis extends along the length of the imaging table, as shown in FIG. 2. For simplicity of illustration, a four-row system is illustrated. The shaded boxes 6 show the reconstruction windows for the cardiac images. These boxes 6, therefore, depict a unique set of time intervals and z-locations. The width of each box 6 represents the volume in z that can be covered with reconstructions corresponding to a particular cardiac cycle. The adjacent set of reconstructions take place only after the heart reaches the same cardiac phase in the next cardiac cycle. If the combination of gantry speed and helical pitch is not properly selected, the entire heart volume will not be uniformly covered in the reconstructed images. For example, if the table travels too fast (helical pitch is too high), gaps 8 will be present between adjacent volumes. Although small gaps could be filled by image space interpolation, larger gaps will lead to discontinuities and artifacts in the volume rendered images. This is particularly problematic when considering the variation of heart rate in a typical patient.

Conventional CAI studies are typically carried out with helical pitches between 0.1 and 0.4. Such a helical pitch is commonly used to account for the worst case scenario with regard to timing, i.e. ensure complete volume coverage at specified heart rate for a given reconstruction. This translates to a higher dose to patients since regions exposed to the x-ray radiation are highly overlapped. That is, since typical helical scan x-rays are continuously projected toward the subject, these regions of overlap correspond to regions that are exposed to multiple exposures of x-ray radiation. To reduce dose to the patient during CAI studies, a number of dose reduction techniques have been developed. In one technique, the current to the x-ray tube is modulated such that the current is reduced outside the reconstruction window defined between each heartbeat. While these techniques have an advantageously reduced dose, cardiac imaging remains to be one of the highest x-ray dose applications in CT.

Therefore, it would be desirable to design an apparatus and method for cardiac CT imaging that further reduces x-ray dose as well as improves temporal and spatial resolution of CT images. It would also be desirable to have a method and system that dynamically responds to cardiac irregularities, such as arrhythmia, such that data acquisition is suspended if invalid or unacceptable data is acquired. Additionally, it would be desirable to dynamically adjust to the variation in heart rate during data acquisition.

BRIEF DESCRIPTION OF THE INVENTION

The above-mentioned shortcomings, disadvantages and problems are addressed herein which will be understood by reading and understanding the following specification.

In an embodiment, a CT imaging system includes a gantry having an opening therein to receive a subject to be scanned. The CT imaging system also includes a table in a movable relationship with the gantry. The CT imaging system also includes a controller configured to control relative movement between the subject disposed on the table and the gantry from a first data acquisition position to a second data acquisition position. The controller is also configured to determine a total scan time based on a first time for acquiring imaging data at the first data acquisition position and a second time for transitioning from the first data acquisition position to the second data acquisition position. The controller is also configured to disable data acquisition in an immediately subsequent cardiac cycle and re-enable data acquisition in the cardiac cycle following the immediately subsequent cardiac cycle if the total scan time exceeds one cardiac cycle of the subject.

In another embodiment, a CT imaging system includes a gantry having an opening therein to receive a subject to be scanned. The CT imaging system also includes a table in a movable relationship with the gantry. The CT imaging system also includes a controller configured to control relative movement between the subject disposed on the table and the gantry from a first data acquisition position to a second data acquisition position. The controller is also configured to determine a total scan time based on a first time for acquiring imaging data at the first data acquisition position and a second time for transitioning from the first data acquisition position to the second data acquisition position. The controller is also configured to reduce a level of x-ray radiation in an immediately subsequent cardiac cycle and then increase the level of x-ray radiation in the cardiac cycle following the immediately subsequent cardiac cycle if the total scan time exceeds one cardiac cycle of the subject.

In another embodiment, a method of CT imaging includes determining a total scan time and if the total scan time exceeds one cardiac cycle of a subject, then disabling data acquisition in an immediately subsequent cardiac cycle and re-enabling data acquisition in the cardiac cycle following the immediately subsequent cardiac cycle. The method of CT imaging also includes positioning one or both of the subject and a gantry at a first data acquisition position and acquiring a dataset of gated CT data from a volume of interest of the subject. The method of CT imaging also includes determining if the dataset is valid. The method of CT imaging also includes positioning one or both of the subject and the gantry at a second data acquisition position different from the first data acquisition position if the dataset is valid. The method of CT imaging also includes re-acquiring the dataset of gated CT data from the volume of interest of the subject at the first data acquisition position if the dataset is invalid.

In another embodiment, a method of CT imaging includes determining a total scan time and if the total scan time exceeds one cardiac cycle of a subject, then reducing a level of x-ray radiation in an immediately subsequent cardiac cycle and then increasing the level of x-ray radiation in the cardiac cycle following the immediately subsequent cardiac cycle. The method of CT imaging also includes positioning one or both of the subject and a gantry at a first data acquisition position and acquiring a dataset of gated CT data from a volume of interest of the subject. The method of CT imaging also includes determining if the dataset is valid. The method of CT imaging also includes positioning one or both of the subject and the gantry at a second data acquisition position different from the first data acquisition position if the dataset is valid. The method of CT imaging also includes re-acquiring the dataset of gated CT data from the volume of interest of the subject at the first data acquisition position if the dataset is invalid.

In another embodiment, a CT imaging system includes a gantry having an opening therein to receive a subject to be scanned. The CT imaging system also includes a table in a movable relationship with the gantry. The CT imaging system also includes a controller configured to determine a number of data acquisition positions to scan the volume of interest of the subject. The controller is also configured to non-sequentially traverse the number of data acquisition positions. The controller is also configured to control relative movement between the gantry and the subject disposed on the table to position the subject in a first data acquisition position. The controller is also configured to coordinate the acquisition of imaging data from the subject at the first data acquisition position with a physiological signal of the subject. The controller is also configured to control relative movement between the gantry and the subject disposed on the table to position the subject in a second non-sequential data acquisition position different from the first data acquisition position only if the imaging data acquired at the first data acquisition position is deemed acceptable.

Various other features, objects, and advantages of the invention will be made apparent to those skilled in the art from the accompanying drawings and detailed description thereof.

BRIEF DESCRIPTION OF THE DRAWINGS

FIG. 1 is a plot of time versus detector row location in z illustrating the coverage gap that is possible with a conventional cardiac CT acquisition;

FIG. 6 is a schematic of an exemplary ECG signal;

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 2:
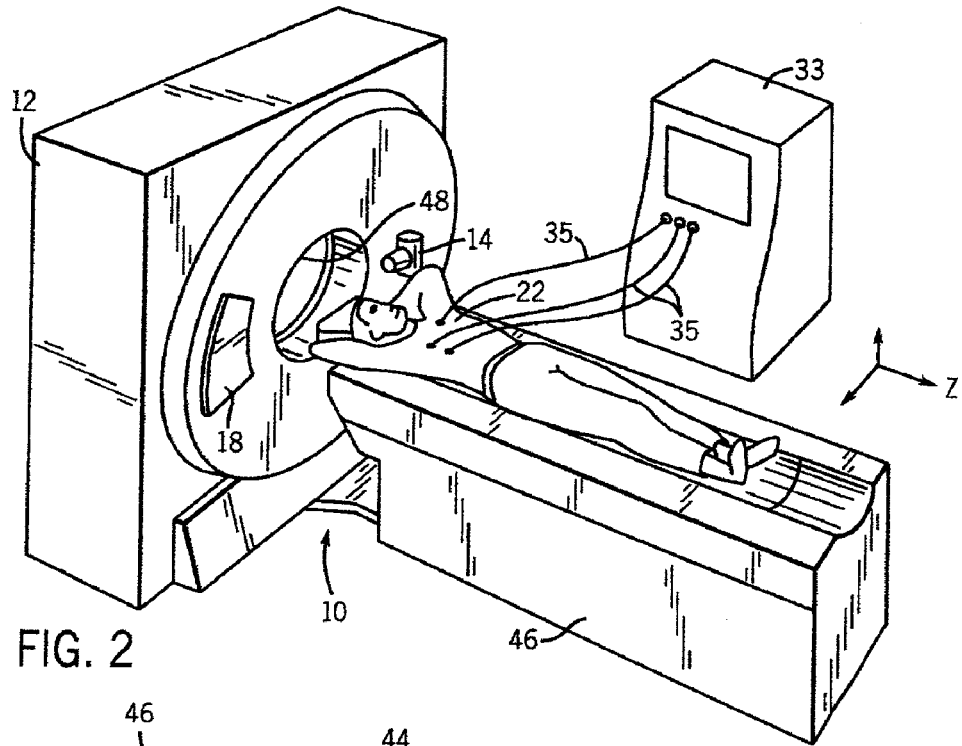
FIG. 2 is a perspective view of a CT system in accordance with an embodiment.
Figure 3:
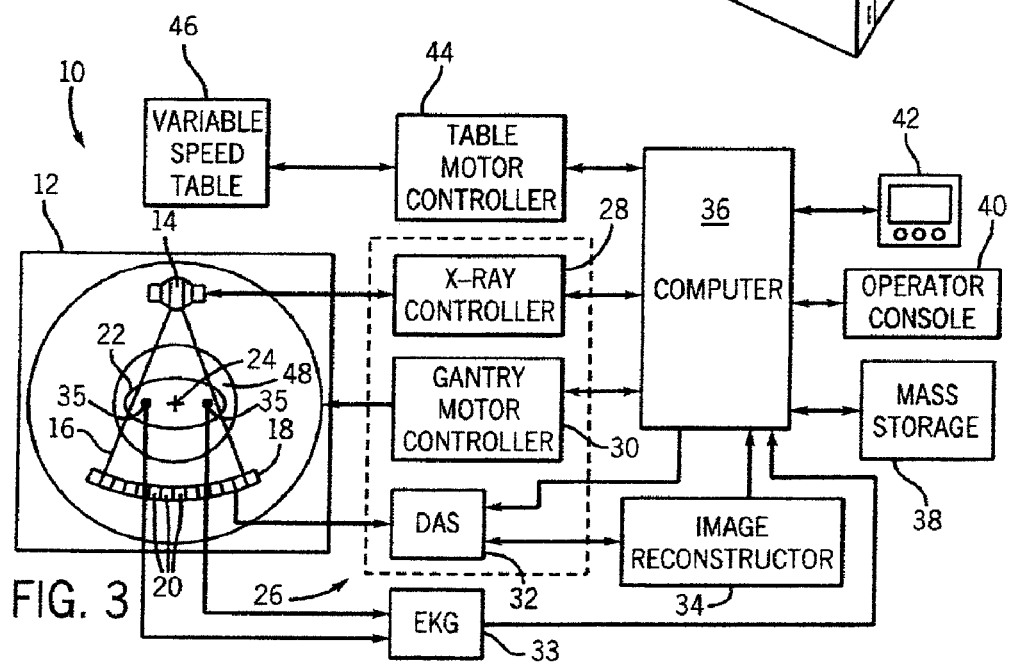
FIG. 3 is a block schematic diagram of the system illustrated in FIG. 2.

Referring to FIGS. 2 and 3, a computed tomography (CT) imaging system 10 is shown as including a gantry 12 having an x-ray source 14 that projects a beam of x-rays 16 toward a detector array 18 on the opposite side of the gantry 12. Detector array 18 is formed by a plurality of detectors 20 that together sense the projected x-rays that pass through a subject or patient 22. In a preferred embodiment, detector array 18 has 64 rows of detectors for the acquisition of 64 slices of data in a single gantry rotation. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. According to an embodiment, the gantry motor controller 30 may control both the rotation and the translation of the gantry 12. A data acquisition system (DAS) 32 in control mechanism 26 samples analog data from detectors 20 and converts the data to digital signals for subsequent processing. As will be described below, computer 36 also receives ECG signals from an ECG 33 connected to the subject via leads 35 to acquire cardiac data of the subject 22. The computer 36 correlates the ECG signals to determine the phases of the cardiac region. Preferably, the ECG machine 33 obtains an ECG recording of the patient before scanning commences such that data acquisition can be timed to occur during quiescent periods between peaks of a cardiac cycle. During these quiescent periods, the heart is relatively still and, therefore, it is preferred for data acquisition to occur during these portions of the cardiac cycle to minimize motion artifacts in the final reconstructed image. An image reconstructor 34 receives sampled and digitized x-ray data from DAS 32 and performs high-speed reconstruction. The reconstructed image is applied as an input to a computer 36 that stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, ECG monitor 33, and gantry motor controller 30. In addition, according to an embodiment, computer 36 operates a table motor controller 44 that controls a motorized table 46 to position patient 22 and gantry 12. Particularly, table 46 moves portions of patient 22 through a gantry opening 48.

An embodiment includes the table 46 in a movable relationship with the gantry 12. The movable relationship could entail the motorized table 46 that is adapted for movement with respect to the gantry 12. The moveable relationship could also entail a gantry 12 adapted for movement with respect to a subject 22 on a stationary table (not shown). Additionally, the table in the movable relationship with the gantry could also entail movement from both the gantry 12 and the table 46. The computer 36 may control the position of the gantry 12 with respect to the subject 22 disposed on the table 46 by the following non-limiting list of options: controlling the movement of the subject 22 disposed on the table 46; controlling the movement of the gantry 12; and controlling both the movement of the table 46 and the movement of the gantry 12.

The present invention is directed to a technique of cardiac CT imaging applicable with the system illustrated in FIGS. 2-3, or equivalents thereof.

In conventional cardiac CT imaging, a helical scan is used. Helical scans are commonly employed because they advantageously eliminate an inter-scan delay. That is, with a helical scan, x-ray projection toward the subject is continuous as is table translation through the opening in the gantry. As a result, helical scans are generally not well-suited for physiological gated scans, such as cardiac imaging, as a result of the lack of flexibility to independently select acquisition location and timing. In helical scans, the table is translated or indexed at a constant speed. This has been shown to be problematic for patients that experience a variation in heart rate during data acquisition.

Figure 4:
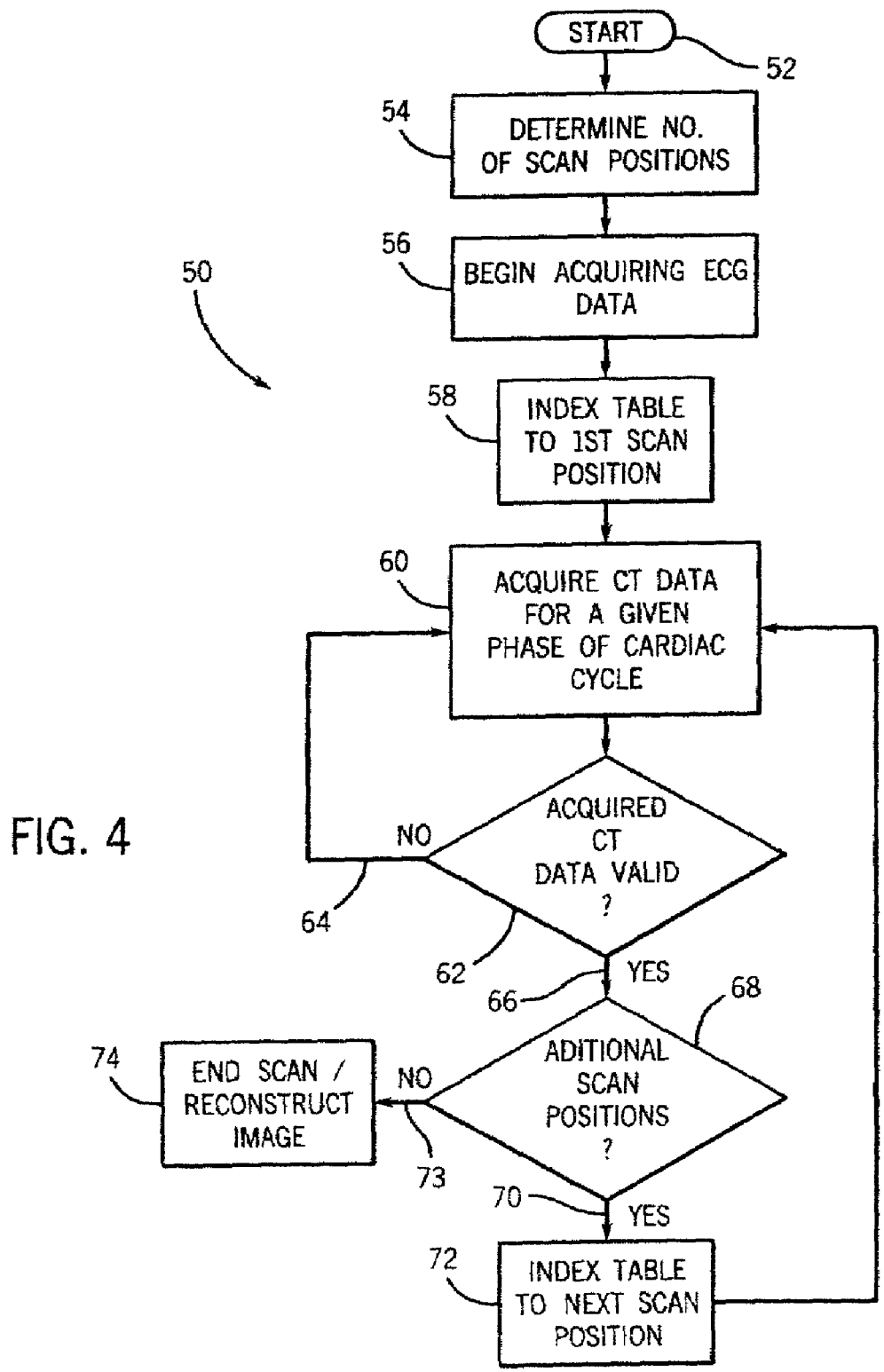
FIG. 4 is a flow chart setting forth the steps of a cardiac CT data acquisition in accordance with an embodiment.

Referring now to FIG. 4, a technique 50 to incrementally step a subject through a number of discrete scan positions in accordance with one embodiment of the present invention will be described. For the purposes of this disclosure, the term "scan position" is defined to include the relative positioning of the gantry and the subject. The scan position will affect the portion of the subject's anatomy that is being imaged. The scan position may, for example, include the relative position of the subject and the gantry in a z-direction, as is known by those skilled in the art. Additionally, for the purposes of this disclosure, the terms "scan position" and "data acquisition position" will be used interchangeably. The technique of FIG. 4 will be described with respect to cardiac imaging, but is applicable with other physiologically gated acquisitions. One skilled in the art will appreciate that the technique illustrated in FIG. 4 may be embodied in the set of instructions of a computer program that may be executed by one or more processors of the CT system. Additionally, the computer program may be stored on a computer readable storage medium, such as a CD, or embodied in a computer data signal that is downloadable to a CT system.

Technique 50 begins at 52 with the prescription of a cardiac CT scan. In this regard, electrodes of an ECG monitor are attached to the subject and the subject is properly positioned on the table that is designed to move the subject fore and aft through the opening defined within the gantry. According to alternate embodiments, moving to the different scan positions may be effected through moving one or both of the gantry and the table. Based on the prescription identified at 52, a number of discrete scan positions is determined at 54. For example, for a CAI study, the number of discrete scan positions would be typically four or five positions for 40 mm detector coverage. That is, the entire volume of the heart of a subject can, typically, be scanned in four or five scan positions. ECG data is continuously acquired throughout the acquisition starting at 56 from the subject. As described above, the computer of the CT system then correlates the ECG signals to determine the phases of the subject's heart motion. In this regard, it is preferred that reading and analysis of the ECG recordings of the subject begins before scanning commences so that data acquisition can be timed to occur between peaks of a cardiac cycle. During these relatively quiet periods, the heart is still and it is, therefore, preferred for data acquisition to occur during these portions of the cardiac cycle to minimize motion artifacts. Thereafter, the table having the scan subject disposed thereon is indexed to the first scan position 58. It should be appreciated that in alternate embodiments the step of indexing the table to the first scan position 58 could be replaced with an equivalent step where either just the gantry or a combination of the gantry and the table are moved to relatively position the subject and the gantry at the first scan position. Thereat, CT data is acquired for a given phase of the cardiac cycle 60.

Once data is acquired for the given phase of cardiac cycle with the subject positioned at the first scan position, a determination is made as to whether the acquired CT data is valid 62. If valid data is not acquired 62, 64, technique 50 returns to step 60 with the reacquisition of data for the given phase of the cardiac cycle with the subject still positioned at the first scan position. However, if valid CT data is acquired 62, 66, then technique 50 proceeds to step 68 and determines if additional scan positions remain 68. If so 68, 70, the table is indexed to the next scan position 72 whereupon data is acquired for the given phase of cardiac cycle with the subject positioned at the next scan position. It should be appreciated that in alternate embodiments, the step of indexing the table to the next scan position could be replaced with an equivalent step where either just the gantry or a combination of the gantry and the table are moved to relatively position the subject and the gantry at the next scan position. However, if data has been acquired for all scan positions 68, 73, the scan ends at 74 with reconstruction of an image.

Technique 50, as described above, is directed to the acquisition of gated CT data from a cardiac region of a subject whereby the incremental change in relative position of the gantry and the table allow for the acquisition of data from a number of scan positions. In contrast to conventional gated acquisitions, relative motion between the table and the gantry is discontinuous. That is, data is acquired from the subject at a first scan position and a determination is made to determine if the data is valid. If the data is valid, the relative position between the table and the gantry is advanced to the next discrete scan position. If the acquired data is invalid, then the relative position between the gantry and the table remains fixed at the current scan position and data is reacquired. In this regard, the CT system does not proceed to the next scan position until valid data is acquired for the current scan position.

Additionally, in a preferred embodiment, x-ray projection toward the subject only occurs during data acquisition. That is, during the intervals in which the table is moved from one scan position to the next scan position, it is preferred that x-ray projection be disabled. In this regard, as data is not acquired during translation of the table, x-ray exposure to the subject does not occur during translation of the table. In this regard, technique 50 advantageously further reduces patient exposure to radiation when compared to conventional helical gated acquisitions. According to another embodiment, the x-ray projection toward the subject may be reduced to a lower level during the intervals in which the table is moved from one scan position to the next scan position.

Figure 5:
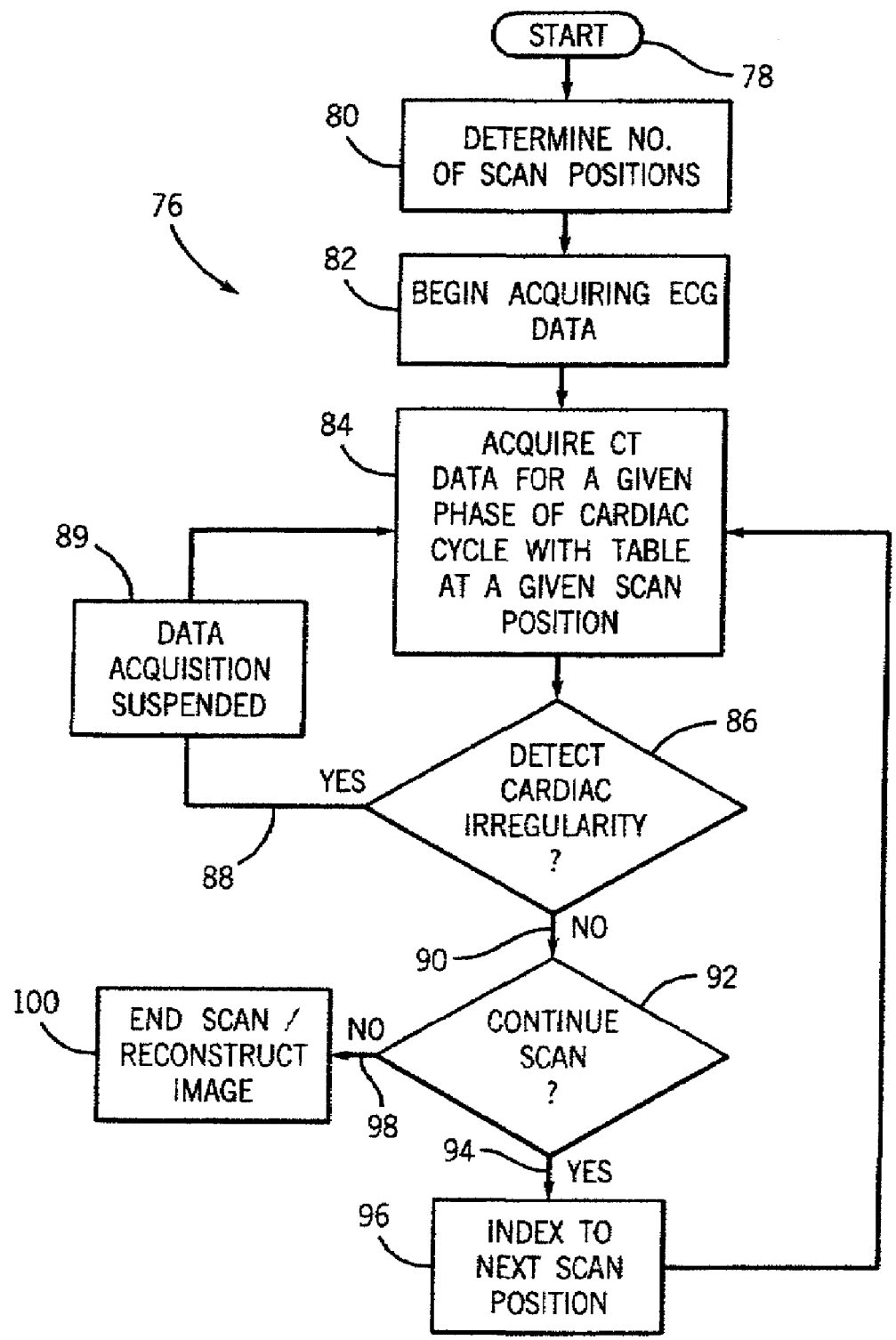
FIG. 5 is a flow chart setting forth the steps of a cardiac CT data acquisition in accordance with an embodiment.

Referring now to FIG. 5, not only is the present invention directed to a technique, such as that described in FIG. 4 that incrementally translates a subject to a number of discrete scan positions, the present invention also includes a technique 76 for interrupting or suspending data acquisition at a given scan position based on a detected irregularity or abnormality in the received ECG signals. While technique 76 will be described independent of the technique described with respect to FIG. 4, one skilled in the art will appreciate that technique 76 may be carried out in conjunction with technique 50 of FIG. 4. Technique 76 begins at step 78 with the prescription of a cardiac CT scan. Thereafter, based on the scan parameters identified at step 78, a number of discrete scan positions is determined at 80. As discussed above, to image the heart of a typical patient, four or five discrete scan positions are needed. Similar to the technique of FIG. 4, ECG data is acquired at 82 prior to the commencement of the CT scan. The acquired ECG data is used by the CT system to correlate the acquisition of CT data from a given phase of the cardiac cycle. One skilled in the art will appreciate, however, that ECG signals are also acquired during the acquisition of CT data. CT data is acquired 84 for a given phase of the cardiac cycle with the subject positioned at a given scan position. While the CT data is being acquired 84, the received ECG signals are monitored to determine if any cardiac irregularities have occurred 86. If so, 86, 88, data acquisition for the given scan position is suspended at 89. In this regard, the acquisition of data for the given phase of the cardiac cycle from the subject will recommence in the next cardiac cycle. If a cardiac irregularity is not detected 86, 90, technique 76 proceeds to step at 92 and determines whether the scan should continue 92, i.e. additional scan positions remain. If so 92, 94, the table is indexed to the next scan position at 96 whereupon data is acquired for the given phase of the cardiac cycle of the subject at the next scan position. Other embodiments may replace step 96 with an equivalent step where movement to the next scan position is created by either moving the gantry or moving a combination of the gantry and the table. Steps 84 through 92 are then re-executed until data has been acquired for all scan positions. Once data has been acquired for all scan positions 92, 98, technique 76 proceeds to step 100 where the scan ends and an image is reconstructed 100.

Referring now to FIG. 6, an exemplary ECG signal 102 is shown. ECG signal 102 graphically illustrates movement of the heart of a subject during a cardiac cycle. As illustrated, the cardiac cycle, i.e., heartbeat, is typically defined by a pair of R-peaks 104. In this regard, a single heartbeat is characterized by an R-R interval 105. As described above, the present invention advantageously reduces x-ray dose to the patient. This is achieved by defining a data acquisition window 106 within each R-R interval 105. As such, x-rays are projected toward the subject only during the data acquisition window 106. In this regard, x-ray emission is disabled during other periods of the R-R interval 105. One skilled in the art will appreciate that the data acquisition window 106 corresponds to the phase of the heart during which data acquisition is to occur. As such, during those phases of the cardiac cycle in which data acquisition is not to occur, the x-ray tube is controlled not to project x-rays toward the subject. Moreover, since data acquisition, timing, and location can be treated independently, gating is more effective. Additionally, even for the case in which all cardiac phases need to be acquired and reconstructed, the acquisition ensures that an overlap of x-ray exposure is not required in the covered regions. That is, all the regions are scanned only once which is in contrast to low-pitch helical acquisitions where the majority of the scan volume is scanned multiple times. Testing has shown that a 67% to 83% reduction in dose can be expected with the present invention when compared to conventional low-pitch helical scans.

Figure 7:
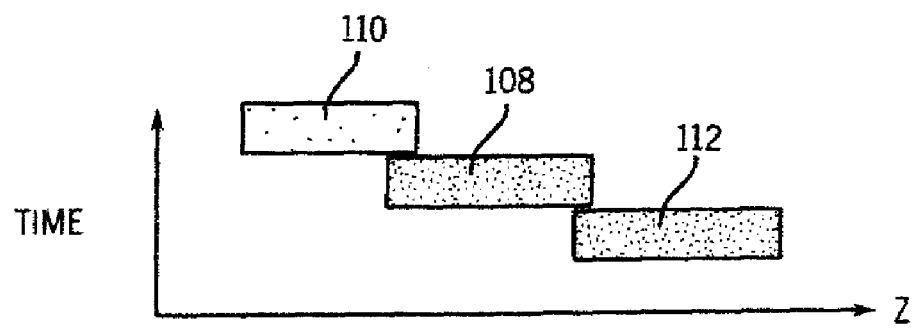
FIG. 7 is a schematic illustrating overlapping data acquisition regions in accordance with an embodiment.

Referring now to FIG. 7 and in accordance with another embodiment of the present invention, overlapping data acquisitions are used to reduce artifacts. Data acquisition 108 overlaps partially with data acquisition 110 and data acquisition 112. This overlapping is exploited to address two major challenges in cardiac imaging: inconsistent heart rate and cone beam. That is, in a typical patient, heart rate varies. Even at a relatively constant heart rate 108, 110, 112, heart motion does not exactly replicate cycle to cycle. Since data acquisitions 108, 110, 112 take place in different cardiac cycles, if not addressed, inconsistency between the heart cycles can lead to shifted boundaries. In addition, for cone beam data acquisitions, some cone beam related artifacts can be present in the images. As such, the overlapped region 108 provides a tool to "blend" regions 108-112 together in a more consistent manner. This blending can take place either during the reconstruction or after reconstruction of an image.

Figure 8:
FIG. 8 is a schematic representation of an exemplary ECG signal illustrating data acquisition time and inter-scan delay relative to a given cardiac cycle.

In yet another embodiment and referring to FIG. 8, gantry speed, inter-scan delay, and coverage are determined based on the patient heart rate, schematically illustrated by ECG signal 114. For the step-and-shoot acquisition described herein, the total scan time is defined by the data acquisition time and the inter-scan delay. The data acquisition time 116 is the time used to collect data and the inter-scan delay 118 is the time used to move one or more of the subject, the table, and the gantry to the next location and ready the patient for scanning. According to an embodiment, the data acquisition time may be the time it takes to acquire CT data at a first data acquisition position and the inter-scan delay may be the time it takes to transition from the first data acquisition position to a second data acquisition position. The transition from the first data acquisition position to the second data acquisition position may be effected by moving one or more of the subject, the table, and the gantry. When the total scan time is less than a patient heart cycle, the next scan can start without any gap in the patient heart cycle. If the total scan time is larger than the heart cycle, scanning cannot start at the next heart cycle. This next heart cycle must be skipped. If the total scan time is larger than two cardiac cycles, two idle cycles will be present in which no data acquisition takes place. The idle cycle where data acquisition does not occur may comprise either a period of time during which no x-ray radiation is projected towards the subject or a period of time during which a reduced level of x-ray radiation is projected towards the subject. For the purposes of this disclosure, "a reduced level of x-ray radiation" is defined to include either a lower average level of x-ray radiation or a lower peak level of x-ray radiation. By changing the gantry scan speed (changing the data acquisition time) and the amount of distance between data acquisition positions (changing the inter-scan delay) the total scan time can be modified so that a minimum time is spent at idle. If it is necessary to reduce the distance between data acquisition positions, then pre-patient collimation may be changed to reduce x-ray dose to patient. That is, if the largest distance between data acquisitions that fits within a single cardiac cycle is 35 mm, x-ray coverage must be reduced by collimating down the primary x-ray beam to 35 mm, i.e. from 35 mm to 40 mm, so that additional dose is not applied to patient.

Figure 9:
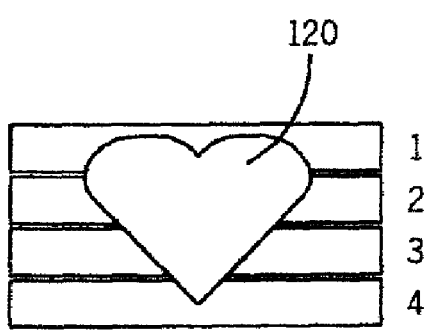
FIG. 9 is a schematic illustrating sequential scanning of a heart in a conventional manner.
Figure 10:
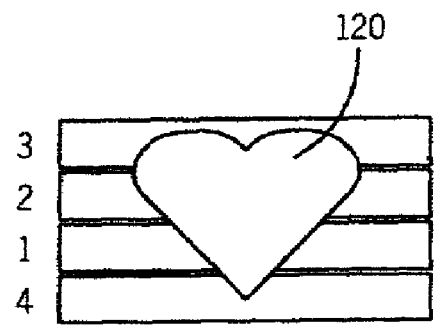
FIG. 10 is a schematic illustrating non-sequential scanning of a heart in accordance with an embodiment.

Referring now to FIGS. 9 and 10 of the present invention, in another embodiment, the entire heart can be scanned "out of sequence", to reduce total acquisition time and/or improve image quality. For example, in a conventional acquisition, the heart 120 is covered sequentially from top to bottom, as illustrated in FIG. 9. However, for a given scan, it may be advantageous to start from a middle or top location and skip a location to scan another part for contrast optimization as illustrated in FIG. 10.

Additionally, it is contemplated that different parts of the heart can be scanned in slightly different cardiac phases. It is well known that the entire heart does not move in complete synchrony. As such, the best resting phase for the right atrium may not be the best location for the left ventricle. Accordingly, the present invention allows each location to be acquired independently. As such, modification can be made to tailor the acquisition to the anatomy. It should be understood that while the heart was used as an exemplary organ, it would be possible to use this technique to acquire imaging data from other volumes of interest as well. It could be used to acquire imaging data of additional organs or of a larger section of the subject's anatomy, such as, for example, the subject's chest. Additionally, it should be understood that the technique of scanning an portion of the subject's anatomy could be gated to additional physiological signals. Two nonlimiting examples of additional physiological signals that could be used to coordinate the acquisition of imaging data include respiratory signals and peristaltic signals.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A CT imaging system comprising:
   a gantry having an opening therein to receive a subject to be scanned;
   a table in a movable relationship with the gantry; and
   a controller configured to:
      control relative movement between the subject disposed on the table and the gantry from a first data acquisition position to a second data acquisition position;
      determine a total scan time based on a first time for acquiring imaging data at the first data acquisition position and a second time for transitioning from the first data acquisition position to the second data acquisition position; and
      if the total scan time exceeds one cardiac cycle of the subject, then disable data acquisition in an immediately subsequent cardiac cycle and re-enable data acquisition in the cardiac cycle following the immediately subsequent cardiac cycle.

2. The CT imaging system of claim 1, wherein the controller is further configured to reacquire data from the first data acquisition position if the data from the first data acquisition position is not deemed acceptable.

3. The CT imaging system of claim 1, wherein the controller is further configured to coordinate an acquisition of imaging data from the subject at the first data acquisition position with a cardiac cycle of the subject.

4. The CT imaging system of claim 1, wherein the controller is further configured to advance the subject to the second data acquisition position only if the imaging data acquired at the first data acquisition position is deemed acceptable.

5. The CT imaging system of claim 1, wherein the controller is further configured to adjust a gantry scan speed based on a heart rate of the subject.

6. The CT imaging system of claim 1, wherein the controller is further configured to adjust a distance between the first data acquisition position and the second data acquisition position based on a heart rate of the subject.

7. The CT imaging system of claim 1, wherein the controller configured to control relative movement is further configured to move the gantry from the first data acquisition position to the second data acquisition position.

8. The CT imaging system of claim 1, wherein the controller configured to control relative movement is further configured to move both the subject disposed on the table and the gantry from the first data acquisition position to the second data acquisition position.

9. A CT imaging system comprising:
   a gantry having an opening therein to receive a subject to be scanned;
   a table in a movable relationship with the gantry; and
   a controller configured to:
      control relative movement between the subject disposed on the table and the gantry from a first data acquisition position to a second data acquisition position;
      determine a total scan time based on a first time for acquiring imaging data at the first data acquisition position and a second time for transitioning from the first data acquisition position to the second data acquisition position; and
      if the total scan time exceeds one cardiac cycle of the subject, then reduce a level of x-ray radiation in an immediately subsequent cardiac cycle and then increase the level of x-ray radiation in the cardiac cycle following the immediately subsequent cardiac cycle.

10. The CT imaging system of claim 9, wherein the controller configured to control relative movement is further configured to move the gantry from the first data acquisition position to the second data acquisition position.

11. The CT imaging system of claim 9, wherein the controller configured to control relative movement is further configured to move both the subject disposed on the table and the gantry from the first data acquisition position to the second data acquisition position.

12. The CT imaging system of claim 9, wherein the controller is further configured to adjust a gantry scan speed based on a heart rate of the subject.

13. The CT imaging system of claim 9, wherein the controller is further configured to adjust a distance between the first data acquisition position and the second data acquisition position based on a heart rate of the subject.

14. The CT imaging system of claim 9, wherein the controller is further configured to coordinate acquisition of imaging data from the subject at the first data acquisition position with a cardiac cycle of the subject.

15. The CT imaging system of claim 9, wherein the controller is further configured to advance the subject to the second data acquisition position only if the imaging data acquired at the first data acquisition position is deemed acceptable.

* * * * *